(12) United States Patent
Shields et al.

(10) Patent No.: US 7,879,336 B2
(45) Date of Patent: *Feb. 1, 2011

(54) VACCINES AND METHODS TO TREAT CANINE INFLUENZA

(75) Inventors: Shelly L. Shields, Plainwell, MI (US); Hans A Draayer, Kalamazoo, MI (US); Michael J Huether, Kalamazoo, MI (US)

(73) Assignee: Pharmacia & Upjohn Company, LLC, Kalamazoo, MI (US)

( * ) Notice: Subject to any disclaimer, the term of this patent is extended or adjusted under 35 U.S.C. 154(b) by 26 days.

This patent is subject to a terminal disclaimer.

(21) Appl. No.: 12/144,304

(22) Filed: Jun. 23, 2008

(65) Prior Publication Data

US 2008/0254063 A1 Oct. 16, 2008

Related U.S. Application Data

(63) Continuation of application No. 11/544,841, filed on Oct. 6, 2006, now Pat. No. 7,722,884.

(60) Provisional application No. 60/724,827, filed on Oct. 7, 2005.

(51) Int. Cl.
| | |
|---|---|
| A01N 65/00 | (2009.01) |
| A01N 63/00 | (2006.01) |
| A61K 39/38 | (2006.01) |
| A61K 39/12 | (2006.01) |
| A61K 39/145 | (2006.01) |
| A61K 39/295 | (2006.01) |
| A61K 39/02 | (2006.01) |
| C12N 7/04 | (2006.01) |
| A61K 39/125 | (2006.01) |

(52) U.S. Cl. ............. 424/201.1; 424/184.1; 424/204.1; 424/93.6; 424/93.1; 424/209.1; 424/234.1; 424/828; 435/236

(58) Field of Classification Search ........................ None
See application file for complete search history.

(56) References Cited

U.S. PATENT DOCUMENTS

| | | |
|---|---|---|
| 6,177,082 B1 | 1/2001 | Dowling et al. |
| 6,436,408 B1 | 8/2002 | Dowling et al. |
| 2004/0039156 A1 | 2/2004 | Segal et al. |
| 2005/0089533 A1* | 4/2005 | Frantz et al. ............. 424/234.1 |
| 2005/0175985 A1 | 8/2005 | Dowling et al. |
| 2006/0153871 A1 | 7/2006 | Olsen et al. |
| 2007/0048819 A1 | 3/2007 | Minke et al. |
| 2007/0048821 A1 | 3/2007 | Minke et al. |
| 2007/0053933 A1 | 3/2007 | Sheppard |
| 2007/0092537 A1 | 4/2007 | Chiang et al. |
| 2007/0098742 A1 | 5/2007 | Yoon et al. |

FOREIGN PATENT DOCUMENTS

| | | |
|---|---|---|
| EP | 1024827 | 2/2007 |
| WO | 0009702 | 2/2000 |
| WO | 2004011651 | 2/2004 |
| WO | 2006088481 | 8/2006 |
| WO | 2006116082 | 11/2006 |
| WO | 2007023287 | 3/2007 |
| WO | 2007024947 | 3/2007 |
| WO | 2007048086 | 4/2007 |

OTHER PUBLICATIONS

Crawford et al., "Transmission of Equine Influenza Virus to Dogs", Science, 2005, vol. 310, pp. 482-485.
Dubovi et al., "Isolation of Equine Influenza Virus from Racing greyhounds with Fatal Hemorrhagic Pneumonia", 47th Annual Meeting of the American Association of Veterinary Laboratory Diagno, Oct. 2004, p. 158.
Karaca et al., "Evaluation of the ability of canarypox-vectored equine influenza virus vaccines to induce humoral immune responses against canine influenza viruses in dogs", AJVR, 2007, vol. 68, No. 2, pp. 208-212.
Crawford et al., "Crossreactivity of Canine and Equine Influenza Antibodies", 24th Annual American College of of Veterinary Internal Medicine Forum, May 31, 2006, p. 711.
Peek et al., "Acute Respiratory Distress Syndrome and Fatal Interstitial Pneumonia Associated with Equine Influenza in a Neonatal Foal", J Vet Intern Med, 2004, vol. 18, No. 1, pp. 132-134.
Yoon et al., "Influenza Virus Infection in Racing Greyhounds", Emerging Infectious Diseases, 2005, vol. 11, No. 12, pp. 1974-1976.
Veterinary Advisory, Aug. 12, 2005, Canine Influenza Virus (Canine Flu) Downloaded from http://www.vetmed.ufl.edu/pr/nw_story/CANINEFLUFACTSHEET.htm on Jan. 10, 2008.
Canine Influenza Backgrounder, Feb. 14, 2007 American Veterinary Medical Association, Downloaded from http://www.avma.org/public_health/influenza/canine_bgnd.asp on Jan. 10, 2008.
Horne et al., "The effects of the use of potassium alum adjuvent in vaccines against vibriosis in rainbow trout", *Salmo gairdneri* Richardson, 1984, Journal of Fish Diseases, vol. 7, pp 91-99.
Wood et al., "The standardization of inactivated equine influenza vaccines by single-radial immunodiffusion", Biological Standardization Apr. 1983, vol. 11, No. 2, pp. 133-136.
Enserink, "Epidemiology, Horse flu virus jumps to dogs", Science, Sep. 30, 2005, vol. 309, No. 5744, p. 2147.
Lai et al., "Diverged Evolution of Recent Equine-2 Influenza (H3N8) Viruses in the Western Hemisphere", Arch. Virol., 146:1063-1074 (2001).
Lai et al., "Alternate Circulation of Recent Equine-2 Influenza Viruses (H3N8) from Two Distinct Lineages in the United States", Virus Research., 100:159-164 (2004).

* cited by examiner

*Primary Examiner*—Zachariah Lucas
*Assistant Examiner*—Benjamin P Blumel
(74) *Attorney, Agent, or Firm*—Timothy J. Gumbleton (57) ABSTRACT

The present invention relates to providing new vaccines and treatments for the diseases related to canine influenza virus. It discloses influenza viral antigens, and methods of presenting these antigens to canines, especially dogs. It relates to attenuated and killed vaccines. The present invention relates to experimentally generated canine and equine influenza viruses. invention also includes influenza A, including H3, N8, H3N8, H7N7 and viruses which contain at least one genome segment from an canine or equine influenza virus. The present invention also relates to the use of these viruses in therapeutic compositions to protect canines, dogs in particular, from diseases caused by influenza viruses Figure 1. Geometric Mean Injection Site Reactions of Dogs Vaccinated with Equine Antigen Vaccines Figure 2. Mean Percent Lung Consolidation in Animals Vaccinated with Equine Influenza Virus Vaccines and Challenged with Canine Influenza Virus

VACCINES AND METHODS TO TREAT CANINE INFLUENZA

CROSS-REFERENCE TO RELATED APPLICATIONS

This application is a continuation of U.S. patent application Ser. No. 11/544,841, filed Oct. 6, 2006, now U.S. Pat. No. 7,722,884, which claims the benefit of U.S. Provisional Patent Application No. 60/724,827, filed Oct. 7, 2005, the entire disclosures of both applications are incorporated herein by reference.

FIELD OF INVENTION

The present invention relates to providing new vaccines and treatments for the diseases related to canine influenza virus. It discloses influenza viral antigens, and methods of presenting these antigens to canines, especially dogs. It relates to attenuated and killed vaccines.

The present invention relates to experimentally generated canine and equine influenza vaccines and viruses. The invention also includes influenza A, H3, N8, H3N8, and H7N7 viruses which contain at least one genome segment from a canine or equine influenza virus. The present invention also relates to the use of these viruses in therapeutic compositions to protect canines, dogs in particular, from diseases caused by influenza viruses.

BACKGROUND OF THE INVENTION

Equine influenza virus has been recognized as a major respiratory pathogen in horses since about 1956. Disease symptoms caused by equine influenza virus can be severe, and are often followed by secondary bacterial infections. Two subtypes of equine influenza virus are recognized, namely subtype-1, the prototype being A/Equine/Prague/1/56 (H7N7), and subtype-2, the prototype being A/Equine/Miami/1/63 (H3N8). Presently, the predominant virus subtype is subtype-2, the H3N8 strain. It is now believed that this strain may be infecting canines and it can be quite virulent with canine fatality rates reported in some cases as high as 36%. It is possible that an interspecies transfer of the complete or a portion of the equine influenza virus to the dog resulted in a new canine specific influenza virus associated with acute respiratory disease. See, *Transmission of Equine Influenza to Dogs* (P. C. Crawford et al., Science 310, 482-485 (2005). There is a clear and convincing need for an effective vaccine to treat and prevent this new canine influenza.

SUMMARY OF THE INVENTION

Figure 1:
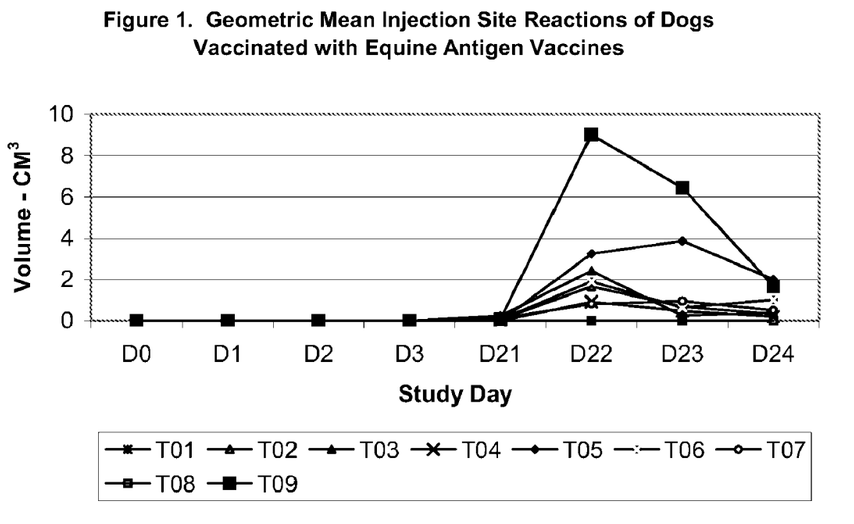
FIG. 1 shows geometric mean injection site reactions of dogs vaccinated with Equine Antigen Vaccines.
Figure 2:
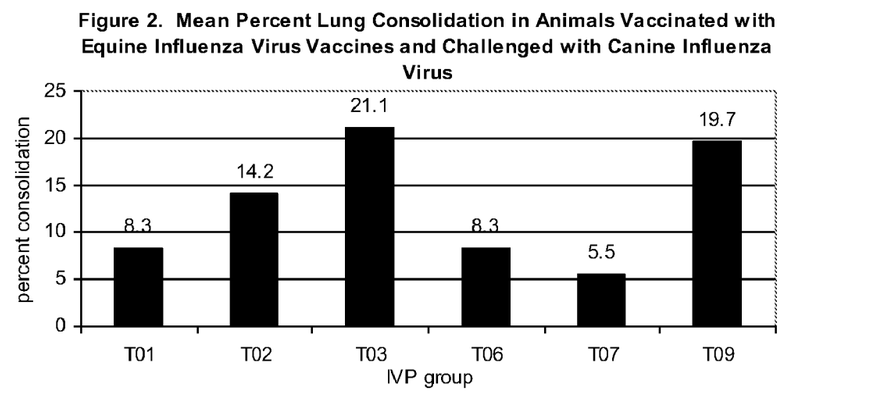
FIG. 2 shows mean percent lung consolidation in animals vaccinated with Equine Influenza Virus Vaccines and challenged with Canine Influenza Virus.

The present invention provides for equine and canine influenza antigens, vaccines, and methods of using those vaccines to treat canines, especially dogs, from infections, disease and symptoms caused by canine influenza. The invention further provides therapeutic compositions to protect an animal against disease caused by influenza virus. Methods of making the vaccines and methods of treating animals are described herein. The antigens of this invention may be any identified influenza virus strain, from any bird or mammal, including but not limited to influenza having the H3N8 antigenic subtype or more commonly referred to as an H3N8 strain. The influenza may be of any mammalian origin, including but not limited to swine, avian, equine or canine origin. Equine and Canine influenza virus and related antigens are preferred. Strains having the proteins designated H3 or N8 are disclosed. Stains having both H3N8 are preferred. Strains having the proteins designated H7N7 are also disclosed.

Antigen concentration and vaccine production are described. Cell culture media and viral growth is described. Vaccine preparation of attenuated, killed and inactivated virus as well as vaccine adjuvants, formulations, forms, and carriers, dosages, routes of administration and assays are all described.

DETAILED DESCRIPTION OF THE INVENTION

Definitions and Abbreviations

The definitions below apply to this disclosure, words not defined have the meaning commonly used by one skilled in the art.

"About," when used in connection with a measurable numerical variable, refers to the indicated value of the variable and to all values of the variable that are within the experimental error of the indicated value (e.g., within the 95% confidence interval for the mean) or within 10 percent of the indicated value, whichever is greater.

"Active immunity" includes both humoral immunity and/or cell-mediated immunity in a dog.

"Antibody" refers to an immunoglobulin molecule that can bind to a specific antigen as the result of an immune response to that antigen. Immunoglobulins are serum proteins composed of "light" and "heavy" polypeptide chains having "constant" and "variable" regions and are divided into classes (e.g., IgA, IgD, IgE, IgG, and IgM) based on the composition of the constant regions. An antibody that is "specific" for a given antigen indicates that the variable regions of the antibody recognize and bind a specific antigen exclusively. Antibodies can be a polyclonal mixture or monoclonal. Antibodies can be intact immunoglobulins derived from natural sources or from recombinant sources, or can be immunoreactive portions of intact immunoglobulins. Antibodies can exist in a variety of forms including, for example, as, Fv, Fab', F(ab')$_2$, as well as in single chains.

"Antigen" or "immunogen" refers to a molecule that contains one or more epitopes (linear, conformational or both) that upon exposure to a subject will induce an immune response that is specific for that antigen. An epitope is the specific site of the antigen which binds to a T-cell receptor or specific antibody, and typically comprises about 3 amino acid residues to about 20 amino acid residues. The term antigen refers to subunit antigens—antigens separate and discrete from a whole organism with which the antigen is associated in nature—as well as killed, attenuated or inactivated bacteria, viruses, fungi, parasites or other microbes. The term antigen also refers to antibodies, such as anti-idiotype antibodies or fragments thereof, and to synthetic peptide mimotopes that can mimic an antigen or antigenic determinant (epitope). The term antigen also refers to an oligonucleotide or polynucleotide that expresses an antigen or antigenic determinant in vivo, such as in DNA immunization applications.

"Antigenicity" refers to the capability of a protein or polypeptide to be immunospecifically bound by an antibody raised against the protein or polypeptide.

"Canine" includes what is commonly called the dog, but includes other members of the family Canidae.

"Cellular Immune Response"—see Immune Response.

"Companion animal", as used herein, refers to any non-human animal in captivity considered to be a pet. These may include, but are not restricted to, dogs, cats, horses, sheep, rabbits, monkeys, and rodents, including mice, rats, hamsters, gerbils, and ferrets.

"Equine" includes what is commonly called the horse, but includes other members of the family Equidae "Excipient" refers to any component of a vaccine that is not an antigen.

"First vaccine," "second vaccine," "third vaccine," and the like, refer to separately administrable vaccines, which may be the same or different, and which in general may be administered in any order. Thus, a third vaccine may be administered to a subject before or after a second vaccine.

"Heterologous", when used herein means derived from a different viral, species or strain.

"Homology", "homologous", and the like, when used herein means the degree of identity shared between polynucleotide or polypeptide sequences.

"Homologous", when used in reference to a viral, species means the same viral species or strain.

"Host cell", when used herein means a bacteria or eukaryotic cell, including mammalian, avian or insect, that harbors a plasmid, virus, or other vector.

"Humoral Immune Response"—see Immune Response.

"Hybridoma"—see Monoclonal Antibody.

"Immune response" in a subject refers to the development of a humoral immune response, a cellular immune response, or a humoral and a cellular immune response to an antigen. A "humoral immune response" refers to one that is mediated by antibodies. A "cellular immune response" is one mediated by T-lymphocytes or other white blood cells or both, and includes the production of cytokines, chemokines and similar molecules produced by activated T-cells, white blood cells, or both. Immune responses can be determined using standard immunoassays and neutralization assays, which are known in the art.

"Immunogenicity" refers to the capability of a protein or polypeptide to elicit an immune response directed specifically against a bacteria or virus that causes the identified disease.

"Immunologically protective amount" or "effective amount to produce an immune response" of an antigen is an amount effective to induce an immunogenic response in the recipient that is adequate to prevent or ameliorate signs or symptoms of disease, including adverse health effects or complications thereof. Either humoral immunity or cell-mediated immunity or both may be induced. The immunogenic response of an animal to a vaccine composition may be evaluated, e.g., indirectly through measurement of antibody titers, lymphocyte proliferation assays, or directly through monitoring signs and symptoms after challenge with wild type strain. The protective immunity conferred by a vaccine can be evaluated by measuring, e.g., reduction in clinical signs such as mortality, morbidity, temperature number and overall physical condition and overall health and performance of the subject. The immune response may comprise, without limitation, induction of cellular and/or humoral immunity. The amount of a vaccine that is therapeutically effective may vary depending on the particular virus used, or the condition of the animal being vaccinated, and can be determined by a veterinary physician.

"Intranasal" administration refers to the introduction of a substance, such as a vaccine, into a subject's body through or by way of the nose and involves transport of the substance primarily through the nasal mucosa.

"Isolated" when used herein means removed from its naturally occurring environment, either alone or in a heterologous host cell, or chromosome or vector (e.g., plasmid, phage, etc.). "Isolated bacteria," "isolated anaerobic bacteria," "isolated bacterial strain," "isolated virus" "isolated viral strain" and the like refer to a composition in which the bacteria or virus are substantial free of other microorganisms, e.g., in a culture, such as when separated from it naturally occurring environment. "Isolated," when used to describe any particularly defined substance, such as a polynucleotide or a polypeptide, refers to the substance that is separate from the original cellular environment in which the substance such as a polypeptide or nucleic acid is normally found. As used herein therefore, by way of example only, a recombinant cell line constructed with a polynucleotide of the invention makes use of the "isolated" nucleic acid. Alternatively if a particular protein or a specific immunogenic fragment is claimed or used as a vaccine it would be considered to be isolated because it had been identified, separated and to some extent purified as compared to how it may exist in nature. If the protein or a specific immunogenic fragment thereof is produced in a recombinant bacterium or eukaryote expression vector that produces the antigen it is considered to exist as an isolated protein or nucleic acid. Example, a recombinant cell line constructed with a polynucleotide makes use of an "isolated" nucleic acid.

"Metabolizable adjuvant" Adjuvants consisting of components that are capable of being metabolized by the target species such as vegetable oil based adjuvants. A Metabolizable adjuvant may be a metabolizable oil. Metabolizable oils are fats and oils that typically occur in plants and animals and usually consist largely of mixtures of triacylglycerols, also known as triglycerides or neutral fats. These nonpolar, water insoluble substances are fatty acid triesters of glycerol. Triacylglycerols differ according to the identity and placement of their three fatty acid residues. Compare to "Non-metabolizable adjuvant"

"Non-metabolizable adjuvant" Adjuvants consisting of components that cannot be metabolized by the body of the animal subject to which the emulsion is administered. Non-metabolizable oils suitable for use in the emulsions of the present invention include alkanes, alkenes, alkynes, and their corresponding acids and alcohols, the ethers and esters thereof, and mixtures thereof. Preferably, the individual compounds of the oil are light hydrocarbon compounds, i.e., such components have 6 to 30 carbon atoms. The oil can be synthetically prepared or purified from petroleum products. Preferred non-metabolizable oils for use in the emulsions of the present invention include mineral oil, paraffin oil, and cyclo-paraffins, for example. The term "mineral oil" refers to a non-metabolizable adjuvant oil that is a mixture of liquid hydrocarbons obtained from petrolatum via a distillation technique. The term is synonymous with "liquefied paraffin", "liquid petrolatum" and "white mineral oil." The term is also intended to include "light mineral oil," i.e., oil which is similarly obtained by distillation of petrolatum, but which has a slightly lower specific gravity than white mineral oil. See, e.g., Remington's Pharmaceutical Sciences, $18^{th}$ Edition (Easton, Pa.: Mack Publishing Company, 1990, at pages 788 and 1323). Mineral oil can be obtained from various commercial sources, for example, J. T. Baker (Phillipsburg, Pa.), USB Corporation (Cleveland, Ohio). Preferred mineral oil is light mineral oil commercially available under the name DRAKEOL®.

"Monoclonal antibody" refers to antibodies produced by a single line of hybridoma cells, all directed towards one epitope on a particular antigen. The antigen used to make the monoclonal antibody can be provided as an isolated protein of the pathogen or the whole pathogen. A "hybridoma" is a clonal cell line that consists of hybrid cells formed by the fusion of a myeloma cell and a specific antibody-producing cell. In general, monoclonal antibodies are of mouse origin; however, monoclonal antibody also refers to a clonal population of an antibody made against a particular epitope of an antigen produced by phage display technology or method that is equivalent to phage display or hybrid cells of non-mouse origin.

"N days" or "M-days" following an event refers, respectively, to any time on the Nth or Mth day after the event. For example, vaccinating a subject with a second vaccine 14 days following administration of a first vaccine means that the second vaccine is administered at any time on the 14th day after the first vaccine.

"ORF" indicates "open reading frame", i.e. the coding region of a gene.

"Oral" or "peroral" administration refers to the introduction of a substance, such as a vaccine, into a subject's body through or by way of the mouth and involves swallowing or transport through the oral mucosa (e.g., sublingual or buccal absorption) or both. Intratracheal is also an oral or peroral administration.

"Oronasal" administration refers to the introduction of a substance, such as a vaccine, into a subject's body through or by way of the nose and the mouth, as would occur, for example, by placing one or more droplets in the nose. Oronasal administration involves transport processes associated with oral and intranasal administration.

"Parenteral administration" refers to the introduction of a substance, such as a vaccine, into a subject's body through or by way of a route that does not include the digestive tract. Parenteral administration includes subcutaneous administration, intramuscular administration, transcutaneous administration, intradermal administration, intraperitoneal administration, intraocular administration, and intravenous administration. For the purposes of this disclosure, parenteral administration excludes administration routes that primarily involve transport of the substance through mucosal tissue in the mouth, nose, trachea, and lungs.

"Pharmaceutically acceptable" refers to substances, which are within the scope of sound medical judgment, suitable for use in contact with the tissues of subjects without undue toxicity, irritation, allergic response, and the like, commensurate with a reasonable benefit-to-risk ratio, and effective for their intended use.

"Pharmaceutically acceptable carrier" refers to a carrier medium that does not interfere with the effectiveness of the biological activity of the active ingredient and is not toxic to the subject to whom it is administered.

"Polyclonal antibody" refers to a mixed population of antibodies made against a particular pathogen or antigen. In general, the population contains a variety of antibody groups, each group directed towards a particular epitope of the pathogen or antigen. To make polyclonal antibodies, the whole pathogen or an isolated antigen is introduced by inoculation or infection into a host that induces the host to make antibodies against the pathogen or antigen.

"Preventing infection" means to prevent or inhibit the replication of the bacteria or virus which cause the identified disease, to inhibit transmission of the bacteria or virus, or to prevent the bacteria or virus from establishing itself in its host, or to alleviate the symptoms of the disease caused by infection. The treatment is considered therapeutic if there is a reduction in bacterial or viral load.

"Protection", "Protecting", and the like, as used herein with respect to a vaccine, means that the vaccine prevents or reduces the symptoms of the disease caused by the organism from which the antigen(s) used in the vaccine is derived. The terms "protection" and "protecting" and the like, also mean that the vaccine can be used to "treat" the disease or one of more symptoms of the disease that already exists in a subject.

"Respiratory" administration refers to the introduction of a substance, such as a vaccine, into a subject's body through or by way of inhalation of a nebulized (atomized) substance. In respiratory administration, the primary transport mechanism involves absorption of the atomized substance through the mucosa in the trachea, bronchi, and lungs and is therefore different than intranasal or peroral administration.

"Specific for," when used to describe antibodies of the invention, indicates that the variable regions of the antibodies of the invention recognize and bind a specific H3N8 strain exclusively (i.e., are able to distinguish a particular H3N8 protein from other known proteins by virtue of measurable differences in binding affinity, despite the existence of localized sequence identity, homology, or similarity between H3N8 proteins and such polypeptides). It will be understood that specific antibodies may also interact with other proteins (or other antibodies in ELISA techniques) through interactions with sequences outside the variable region of the antibodies, and, in particular, in the constant region of the molecule. Screening assays to determine binding specificity of an antibody of the invention are well known and routinely practiced in the art. For a comprehensive discussion of such assays, see Harlow et al. (Eds.), *Antibodies: A Laboratory Manual*; Cold Spring Harbor Laboratory; Cold Spring Harbor, N.Y. (1988), Chapter 6. Antibodies of the invention can be produced using any method well known and routinely practiced in the art.

"Subunit vaccine" refers to a type of vaccine that includes one or more antigens, but not all antigens, which are derived from or homologous to, antigens from a pathogen of interest, such as a virus, bacterium, parasite or fungus. Such a composition is substantially free of intact pathogen cells or pathogenic particles, or the lysate of such cells or particles. Thus, a subunit vaccine can be prepared from at least partially purified, or substantially purified, immunogenic polypeptides from the pathogen or its analogs. Methods of obtaining an antigen or antigens in the subunit vaccine include standard purification techniques, recombinant production, or chemical synthesis. A "Subunit vaccine" thus refers to a vaccine consisting of a defined antigenic component or components of a complete viral, bacterial or other immunogen.

"Specific immunogenic fragment" is meant a portion of a sequence that is recognizable by an antibody that is specific for the sequence.

"Subject" refers to any animal having an immune system, which includes mammals such as dogs.

"$TCID_{5038}$" refers to "tissue culture infective dose" and is defined as that dilution of a virus required to infect 50% of a given batch of inoculated cell cultures. Various methods may be used to calculate $TCID_{50}$, including the Spearman-Karber method which is utilized throughout this specification. For a description of the Spearman-Karber method, see B. W. Mahy & H. O. Kangro, *Virology Methods Manual* 25-46 (1996).

"Therapeutic agent" refers to any molecule, compound, virus or treatment, preferably a virus attenuated or killed, or subunit or compound, that assists in the treatment of a viral infection or a disease or condition caused thereby.

"Therapeutically effective amount," in the context of this disclosure, refers to an amount of an antigen or vaccine that would induce an immune response in a subject (e.g., dog) receiving the antigen or vaccine which is adequate to prevent or ameliorate signs or symptoms of disease, including adverse health effects or complications thereof, caused by infection with a pathogen, such as a virus (e.g., H3N8), bacterium, parasite or fungus. Humoral immunity or cell-mediated immunity or both humoral and cell-mediated immunity may be induced. The immunogenic response of an animal to a vaccine may be evaluated, e.g., indirectly through measurement of antibody titers, lymphocyte proliferation assays, or directly through monitoring signs and symptoms after challenge with wild type strain. The protective immunity conferred by a vaccine can be evaluated by measuring, e.g., reduction in clinical signs such as mortality, morbidity, temperature number and overall physical condition and overall health and performance of the subject. The amount of a vaccine that is therapeutically effective may vary depending on the particular virus used, or the condition of the subject, and can be determined by one skilled in the art.

"Transmitted" means a virus that is capable of being passed from a first animal (dog) to a second animal (dog) where the second dog demonstrates serovonversion to the transmitted virus.

"Treating" refers to reversing, alleviating, inhibiting the progress of, or preventing a disorder, condition or disease to which such term applies, or to preventing one or more symptoms of such disorder, condition or disease.

"Treatment" refers to the act of "treating" as defined immediately above.

"Vaccine" refers to an immunogenic composition selected from a virus, either modified live, attenuated, or killed, or a subunit vaccine, or any combination of the aforementioned. Administration of the vaccine to a subject results in an immune response. The vaccine may be introduced directly into the subject by any known route of administration, including parenterally, perorally, and the like.

Part 1. Antigens and Virus Strains, Their Production, Manufacture, Formulation Into and Administration of Vaccines.

One aspect of the present invention provides vaccines that use the following antigens to provoke an immunogenic response.

Useful Antigen(s) of the invention. The antigens of this invention may be any identified influenza virus strain, from any bird or mammal, including but not limited to, influenza virus having the subtype H3 hemagglutinin and subtype N8 neuraminidase, or the H3N8 subtype or more commonly referred to as an H3N8 virus. The influenza may be of any mammalian or avian origin, including but not limited to swine, equine or canine origin. Equine and canine influenza antigens are preferred. Strains having the subtype glycoproteins designated H3 or N8 and more preferably strains having both H3 and N8.

The strains and variants and mutants and variants thereof are also preferred as described in *Transmission of Equine Influenza to Dogs* (P. C. Crawford et al., Science 310, 482-485 (2005). The viral HA is a critical determinant of host species specificity of influenza virus.

The influenza antigens of this invention can be isolated from dogs, horses, pigs, and fowl both domestic and wild. The animals chosen for sample collection should display acute and/or sub-acute clinical syndromes which may include mild to severe respiratory symptoms and fever. Animals may also exhibit signs of anorexia and lethargy. Methods of virus isolation are well known to those skilled in the art including: inoculating mammalian or avian cell cultures, embryonated eggs with nasal or pharyngeal mucus samples from clinical specimens, collection by swabbing of the nasal passage or throat, or by collecting tissues such as: spleen, lung, tonsil and liver and lung lavage. The cytopathic effect of the virus can be observed in cell culture, and allantoic fluid or cell lysates can be tested for their ability to agglutinate human, rooster, turkey or guinea pig red blood cells, presumptive evidence for the presence of an influenza virus.

Nomenclature of viral strains and possible antigens. Type A influenza virus strains are subdivided into subtypes based on the antigenic characteristics of their glycoproteins on the virion surface. These virus glycoproteins are hemagglutinin (HA) and neuraminidase (NA). Typically the HA subtype is named first and the NA second, thus, H3N8 refers to a virus with hemagglutinin subtype 3 and neuraminidase subtype 8. The subtype is based on serological analysis of the HA and NA. Using the procedures disclosed herein a vaccine for any of these subtypes may be made. Currently there are 16 identified HA subtypes and 9 identified NA subtypes. There may be more in the wild that have not yet been described. Specifically, identified subtypes include H1, H2, H3, H4, H5, H6, H7, H8, H9, H10, H11, H12, H13, H14, H15 and H16 and N1, N2, N3, N4, N5, N6, N7, N8, and N9. All of these combinations of subtypes, and any combination thereof and any subtype and combination of future subtypes that will be identified in the future using the procedures described above or substantially similar procedures are hereby described and claimed as useful antigens of this invention. All other HA and NA combinations of subtypes are disclosed. This includes but is not limited to preferred subtypes H3N8 and H7N7.

The influenza virus hemagglutinin (HA) is the virion surface glycoprotein that attaches the virus to its receptors on host cells and fuses the viral envelope with the membranes of endocytic vesicles to initiate the infectious process. It is also the virion component most important in the stimulation and formation of protective antibodies. The amino acid sequence of the HA and hence the location of its N-glycosylation sites is determined by the viral genome.

The segmented, negative stranded RNA genome of the influenza virus is replicated by an RNA dependent-RNA polymerase which lacks an effective proofreading function, leading to a high rate of transcription errors that can result in amino acid substitutions in surface glycoproteins HA and NA. One of the consequences of this high mutation frequency is that virus populations contain mutants that differ from the majority in the number and position of the N-linked glycans on the HA. The structures of these oligosaccharides may be determined by their position on the HA and by the array of biosynthetic and trimming enzymes provided by the host cell in which the virus is grown. Thus, the plasticity of the viral genome and the host-specified glycosylation machinery can, together, create virus populations that are more heterogeneous in structure and function than could be developed by either process alone. This diversity is considered to be responsible for survival of these viruses in a variety of biological niches and for their ability to overcome the inhibitory effects of neutralizing antibodies and antiviral agents. Mutations in the viral genome of various strains have been identified and those mutated strains are also claimed here. For example, some of these mutants are described in *Transmission of Equine Influenza to Dogs* (P. C. Crawford et al., Science 310, 482-485 (2005) incorporated herein by reference.

This invention also discloses a vaccine made from a specific strain collected and identified as Equine Influenza Strain A/Equine/2/Miami/1/63. This strain is deposited at the American Type Culture Collection, 10801 University Boulevard, Manassas, Va. 20110-2209 as ATCC accession number VR 317. This strain was originally isolated from nasal washings from a sick horse in Miami in 1963. The virus was passaged 5 times in chicken embryos. The virus is further classified as H3N8.

Another example of a North American H3N8 influenza virus derived from a horse is A/Equine/Kentucky/1998. Additional examples of H3N8 derived from a horse are A/Equine/Kentucky/15/2002, A/Equine/Ohio/1/2003, A/Equine/Kentucky/1/1994, A/Equine/Massachusetts/213/2003, A/Equine/Wisconsin/2003 and A/Equine/New York/1999. Other examples are European H3N8 influenza virus derived A/Equine/Newmarket/A2/1993.

This invention also discloses a vaccine made from a specific strain collected and identified as canine Influenza Strain A/canine/Iowa/13628/2005 and Strain A/canine/Iowa/9A1/B5/08/D12. The latter strain, Strain A/canine/Iowa/9A1/B5/08/D12 was deposited as UC 25508, on 29 Jun. 2006 at the American Type Culture Collection, 10801 University Boulevard, Manassas, Va. 20110-2209, the ATCC accession number is PTA-7694. The virus is further classified as H3N8.

In addition to the above strains we disclose a strain obtained in the following manner. Identify a dog or group of dogs exhibiting clinical signs of respiratory disease, obtain samples of oral or nasal secretions or samples derived from respiratory tissue or internal organ tissue from the dogs, assay the samples and identify the presence of an H3N8 influenza virus. Using the procedures described herein, isolate, purify, culture, grow, produce, concentrate this virus antigen and identify as Pfizer canine influenza virus. Adapt to and passage in either embryonated eggs or canine cells or both, identify as Master Seed, canine influenza H3N8 virus. A canine derived H3N8 influenza virus is preferred. An equine or porcine derived H3N8 can also be used as well as an influenza virus of subtype H3 or N8. We disclose a strain obtained in the following manner. Infect a dog or group of dogs with equine influenza H3N8. From dogs exhibiting clinical or subclinical signs of respiratory disease, obtain samples of oral or nasal secretions, or samples derived from respiratory tissue or lung lavage or internal organ tissue from the dogs, assay the samples and identify the presence of an H3N8 influenza virus. Using the procedures described herein, isolate, purify, culture, grow, produce, concentrate this virus antigen and identify as canine influenza virus. Adapt to and passage in either embryonated eggs or canine cells or both, identify as Master Seed, canine influenza H3N8 virus. A canine derived H3N8 influenza virus is preferred. An equine or porcine derived H3N8 can also be used as well as an influenza virus of subtype H3 or N8. The porcine derived H3N8 virus is treated in the same manner as the equine or canine derived virus that is fully described herein.

Part 2. Detailed Descriptions of the Production, Manufacture, Formulation and Administration of Vaccines Produced From the Antigens of Part 1.

Part 2a) Discussion. The virus antigens of Part 1, may be made into useful compositions of matter comprising the virus antigen modified to reduce its virulence and formulated into a useful formulation or vaccine formulation. The following descriptions provide details for the production, manufacture, formulation and administration of vaccines useful for the prevention or treatment of clinical signs associated with influenza virus infection in dogs, or in the prevention of disease in dogs caused by an canine or equine influenza virus. The canine influenza infection to be treated may be caused by equine influenza virus or it may be a new modified canine influenza derived from a equine influenza virus. The treatments described here may act as an aid in the prevention of shedding of canine or equine influenza virus in canine disease.

Described herein are methods and materials for treating and immunizing animals with a vaccine and in particular dog against equine and canine influenza viruses. The method includes administering to the dog a therapeutically effective amount of a first, second and or third vaccine that is capable of inducing an immune response, and in particular in the dog against H3N8 influenza viruses. The vaccine of the present invention is generally intended to be a prophylactic treatment which immunizes dogs against disease caused by virulent strains of equine or canine influenza virus.

Here we disclose vaccines that provide active and or passive immunity. Either the entire vaccine, or specific immunogenic fragments of their proteins, would be expected to be effective when given as a therapeutic treatment against equine or canine influenza viruses. Thus, the immunity that is provided by the present invention can be either active or passive immunity, and the intended use of the vaccine can be either prophylactic or therapeutic. In a preferred embodiment, the vaccine further includes a vaccine for immunizing a dog against any form of a canine or equine influenza virus.

Part 2 b) Vaccine Production and Antigen Concentration. The vaccine described in this section may be produced by growing the selected virus in cells. Production of the virus is preferred in equine or canine mammalian cell culture. Virus (antigen) growth or production in eggs is also preferred. Dog kidney cell lines are preferred. Viral propagation may also be accomplished on any useful media and permissive cell lines, which may be derived from avian or mammalian cell lines derived from feline, equine, bovine or porcine cell lines. The vaccines typically contain between $10^3$ and $10^9$ $TCID_{50}$, levels of virus prior to inactivation. Alternatively the antigen content in the virus preparation could be assayed by the hemagglutination inhibition (HI) test, single radial diffusion or hemagglutination assay and using this assay one would prefer a vaccine with a titer of between 10 to 10,000 HA units/ml, more typically between 100 to 2000 HA units/ml, and frequently between 100 to 1000 HA units/ml as the amount administered per dose.

Virus growth: cell lines and embryonated eggs The preferred cell line for propagation of influenza virus is canine kidney (DK). Other cell lines can be utilized which include primary and immortalized equine kidney (EK), equine dermal (ED), swine testicular (ST), porcine kidney (PK), bovine kidney (BK), feline kidney (FK), Vero and primary and immortalized chicken embryo fibroblasts (CEF). The preferred cell culture system for growing influenza virus is a traditional adherent monolayer culture. Alternatively, suspension and microcarrier cell culture systems can also be utilized. A preferred microcarrier is Cytodex 3 microcarrier beads (Amersham Biosciences Ltd.). Other examples of microcarriers include beads composed of glass, silicone and dextran, DEAE, collagen, dextran or gelatin.

The preferred vessel for culturing cell lines and propagation of influenza virus is the roller bottle, the preferred roller bottle surface area is 1760 cm$^2$ but can range from 490-4250 cm$^2$. Alternatively, other useful cell culture formats include flasks (150 cm$^2$-420 cm$^2$), stacked modules (21,000 cm$^2$-340,000 cm$^2$) and stir tanks (1.0 L-900 L). The preferred multiplicity of infection (MOI) is 0.001-0.1 but can range from 0.0001-2.0. The preferred window to harvest virus from cell culture is day 2 to 5 post-infection, but can range from day 1 to day 7 post-infection.

Virus propagation can also be accomplished by inoculating embryonated eggs. Typically 0-12 day old embryonated eggs are used for virus propagation. Preferably 7-8 day old embryonated eggs are used for virus growth. The virus is inoculated into the amniotic cavity of the egg. The virus replicates in the cells of the amniotic membrane and large quantities are released back into the amniotic fluid. After 2-3 days post inoculation, virus in the amniotic fluid can be harvested.

Cell culture media: Preferred cell culture media formulations to propagate influenza virus includes, but is not limited to, the following: Dulbecco's modified eagle media (DMEM), basal modified eagle media, Optimem and Leibovitz-15 (L-15) media. Typically the cell culture media is supplemented with 0.1 to 10 units of trypsin. Alternatively, plant derived equivalents of trypsin (e.g. Accutase) ranging from 2-100 units can also be used in cell culture for efficient propagation of virus. Cell culture media can be used in the absence or presence of animal-derived components. An example of supplementation with an animal-derived component is gamma-irradiated serum ranging from 0.5-10% final concentration.

Part 2c) Vaccine Preparation Inactivated or Killed, Subunit and Attenuated, Modified-Live.

Inactivated or Killed. In one embodiment of the present invention, the vaccine comprises an inactivated or killed H3N8 influenza virus vaccine comprising an H3N8 equine or canine strain selected from any equine or canine infectious influenza strain. See *Transmission of Equine Influenza to Dogs* (P. C. Crawford et al., Science 310, 482-485 (2005). The vaccine can also be comprised of influenza H3N8 derived from swine or any influenza of subtype H3 or N8. The inactivated vaccine is made by methods well known in the art. For example, once the virus is propagated to high titers, it would be readily apparent to those skilled in the art that the virus antigenic mass could be obtained by methods well known in the art. For example, the virus antigenic mass may be obtained by dilution, concentration, or extraction. All of these methods have been employed to obtain appropriate viral antigenic mass to produce vaccines. The virus may be inactivated by treatment with formalin (e.g. 0.1-10%), betapropriolactone (BPL) (e.g. 0.01-10%), or with binary ethyleneimine (BEI) (e.g. 1-10 mM) which is preferred here, or using other methods known to those skilled in the art. Commonly used conditions and agents are suggested but other agents and concentrations should be apparent to one skilled in the art.

In addition to killed virus production detailed above, various means of attenuation are also possible and are well known and described in the art and applicable here. Attenuation leading to modified live vaccines is also possible. Some of these techniques are described here and below. Among the more preferred forms of attenuation are continuous passaging in cell culture, continuous passaging in animals, various methods for generating genetic modifications and ultraviolet or chemical mutagenesis.

Subunit Vaccines. In addition, equine or canine influenza subunit vaccines can be produced by recombinant expression techniques which include, but are not limited to, heterologous prokaryotic expression (e.g., *E. coli, Pseudomonas, Salmonella* etc.) and heterologous eukaryotic expression (e.g., yeast [*Pichia, Yarrowia*], insect cells [Baculovirus], etc.) and viral vectors (e.g., canine adenovirus, human adenovirus, poxvirus, canine herpesvirus).

Attenuated and Modified-Live. An Attenuated Virus Canine Vaccine is prepared from cell line or egg cultivated influenza virus preferably an influenza derived H3N8, that has been attenuated by serial passage including serial passage at sub-optimal temperatures to a state where it is no longer capable of causing disease, but still capable of eliciting a protective immune response.

Attenuation of an influenza virus may be achieved by serial passaging of a wild-type influenza virus strain in cell culture. The virus strain can be passaged in a variety of cell systems until its ability to produce disease is lost whilst its immunogenic character is fully retained. Once inoculated into the host, the virus may be capable of multiplication to some extent. Suitable attenuated viral strains may also be obtained by serial passaging to obtain an over-attenuated strain. The "over-attenuation" means that the number of passages for attenuation has been substantially greater than what is normally necessary for the removal of pathogenicity. The attenuated virus retains its antigenicity after these numerous passages, for example retaining both its haemagglutinin and neuraminidase antigens, so that its immunogenic ability is not impaired. Such strains produce practically no symptoms or side effects when administered, and thus are safe and efficacious vaccines.

Attenuation of influenza virus may be achieved through cold-adaptation of an influenza virus strain. Cold-adapted influenza virus strains may be produced by methods which includes passaging a wild-type influenza virus, followed by selection for virus that grows at a reduced temperature. Cold-adapted influenza viruses can be produced, for example, by sequentially passaging a wild-type influenza virus in embryonated chicken eggs at progressively lower temperatures, thereby selecting for certain members of the virus mixture which stably replicate at the reduced temperature. A cold-adapted influenza virus strain may exhibit a temperature sensitive phenotype. A temperature sensitive cold-adapted influenza virus replicates at reduced temperatures, but no longer replicates or forms plaques in tissue culture cells at certain higher growth temperatures at which the wild-type virus will replicate and form plaques. A temperature at which a temperature sensitive virus will grow is referred to herein as a "permissive" temperature for that temperature sensitive virus, and a higher temperature at which the temperature sensitive virus will not grow, but at which a corresponding wild-type virus will grow, is referred to herein as a "non-permissive" temperature for that temperature sensitive virus. For example, certain temperature sensitive cold-adapted influenza viruses replicate in embryonated chicken eggs at a temperature at or below about 30° C., and will form plaques in tissue culture cells at a permissive temperature of about 34° C., but will not form plaques in tissue culture cells at a non-permissive temperature of about 37° C. Certain cold-adapted influenza viruses may have a dominant interference phenotype. That is, they dominate an infection when co-infected into cells with another influenza virus, thereby impairing the growth of that other virus. A cold-adapted influenza virus may also be produced through recombinant means. In this approach, one or more specific mutations, associated with identified cold-adaptation, attenuation, temperature sensitivity, or dominant interference phenotypes, are identified and are introduced back into a wild-type influenza virus strain using a reverse genetics approach. Reverse genetics entails using RNA polymerase complexes isolated from influenza virus-infected cells to transcribe artificial influenza virus genome segments containing the mutation(s), incorporating the synthesized RNA segment(s) into virus particles using a helper virus, and then selecting for viruses containing the desired changes.

Part 2 d) Vaccine Adjuvants, Formulations, Forms and Carriers. Components of vaccines presented here will preferably include one or more adjuvants. Adjuvants include, but are not limited to, the RIBI adjuvant system (Ribi Inc.) Aluminum salts, including Alum (0.5-20%, more preferred is less than 10%, more preferred are 2 and 5%), Aluminum phosphate (0.5-20%, more preferred is less than 10%, more preferred are 2 and 5%), Aluminum hydroxide (Alhydrogel or Rehydragel ranging from 0.5-20%, more preferred is less than 10%, more preferred are 2 and 5%), cholesterol, oil-in water emulsions, water-in-oil emulsions such as, e.g., Freund's complete and incomplete adjuvants, Block co-polymer (CytRx, Atlanta Ga.), SAF-M (Chiron, Emeryville Calif.), AMPHIGEN® adjuvant, saponin, and saponins such as, Quil A, QS-21 (Cambridge Biotech Inc., Cambridge Mass.), GPI-0100 (Galenica Pharmaceuticals, Inc., Birmingham, Ala.) with preferred Saponin concentrations of 10-100 microgram and about 50 microgram preferred or other saponin fractions, monophosphoryl lipid A, Avridine lipid-amine adjuvant, heat-labile enterotoxin from *E. coli* (recombinant or otherwise), cholera toxin, or muramyl dipeptide, among many others. The immunogenic compositions can further include one or more other immunomodulatory agents such as, e.g., interleukins, interferons, or other cytokines. The immunogenic compositions can also include gentamicin and Merthiolate.

Components of vaccines may include pharmaceutically acceptable excipients, including carriers, solvents, and diluents, isotonic agents, buffering agents, stabilizers, preservatives, immunomodulatory agents (e.g., interleukins, interferons, and other cytokines), vaso-constrictive agents, antibacterial agents, antifungal agents, and the like. Typical carriers, solvents, and diluents include water, saline, dextrose, ethanol, glycerol, and the like. Representative isotonic agents include sodium chloride, dextrose, mannitol, sorbitol, lactose, and the like. Useful stabilizers include gelatin, albumin, and the like.

H3N8 influenza virus vaccines are provided in various forms, depending on the route of administration, storage requirements, and the like. For example, the vaccines can be prepared as aqueous solutions or dispersions suitable for use in syringes, droppers, nebulizers, etc., or can be prepared as lyophilized powders, which are reconstituted in saline, HEPES buffer, or the aqueous, immunogenic fraction of a second canine vaccine and the like, prior to use.

The vaccine for any one of the embodiments of the present invention is formulated in a pharmaceutically accepted carrier according to the mode of administration to be used. One skilled in the art can readily formulate a vaccine that comprises a live or killed equine or canine influenza or an immunogenic fragment thereof, a recombinant virus or bacterial vector encoding equine or canine influenza, a specific immunogenic fragment thereof, or a DNA molecule encoding equine or canine influenza or a specific immunogenic fragment thereof.

In cases where intramuscular injection is preferred, an isotonic formulation is preferred. Generally, additives for isotonicity can include sodium chloride, dextrose, mannitol, sorbitol, and lactose. In particular cases, isotonic solutions such as phosphate buffered saline are preferred. The formulations can further provide stabilizers such as gelatin and albumin. In some embodiments, a vaso-constrictive agent is added to the formulation. The pharmaceutical preparations according to the present invention are provided sterile and pyrogen-free. However, it is well known by those skilled in the art that the preferred formulations for the pharmaceutically accepted carrier which comprise the vaccines of the present invention are those pharmaceutical carriers approved in the regulations promulgated by the United States Department of Agriculture, or equivalent government agency in a foreign country such as Canada or Mexico or any one of the European nations for any canine vaccine, polypeptide (antigen) subunit vaccines, recombinant virus vector vaccines, and DNA vaccines. Therefore, the pharmaceutically accepted carrier for commercial production of the vaccine of the present invention is a carrier that is already approved or will be approved by the appropriate government agency in the United States of America or foreign country. The vaccine can further be mixed with an adjuvant that is pharmaceutically acceptable. In certain formulations of the vaccine of the present invention, the vaccine is combined with other canine vaccines to produce a polyvalent vaccine product that can protect canine against a wide variety of diseases caused by other canine pathogens.

The vaccine compositions optionally may include vaccine-compatible pharmaceutically acceptable (i.e., sterile and non-toxic) liquid, semisolid, or solid diluents that serve as pharmaceutical vehicles, excipients, or media. Diluents can include water, saline, dextrose, ethanol, glycerol, and the like. Isotonic agents can include sodium chloride, dextrose, mannitol, sorbitol, and lactose, among others. Stabilizers include albumin, among others. Any adjuvant known in the art may be used in the vaccine composition, including metabolizable and non-metabolozable adjuvants, oil-based adjuvants such as Freund's Complete Adjuvant and Freund's Incomplete Adjuvant, mycolate-based adjuvants (e.g., trehalose dimycolate), bacterial lipopolysaccharide (LPS), peptidoglycans (i.e., mureins, mucopeptides, or glycoproteins such as N-Opaca, muramyl dipeptide [MDP], or MDP analogs), proteoglycans (e.g., extracted from *Klebsiella pneumoniae*), streptococcal preparations (e.g., OK432), Biostim™ (e.g., 01K2), the "Iscoms" of EP 109 942, EP 180 564 and EP 231 039, aluminum hydroxide, saponin, DEAE-dextran, neutral oils (such as miglyol), vegetable oils (such as arachis oil), liposomes, and Pluronic® polyols.

The immunogenic compositions of the present invention can be made in various forms depending upon the route of administration. For example, the immunogenic compositions can be made in the form of sterile aqueous solutions or dispersions suitable for injectable use, or made in lyophilized forms using freeze-drying techniques. Lyophilized immunogenic compositions are typically maintained at about 4° C., and can be reconstituted in a stabilizing solution, e.g., saline or/and HEPES, with or without adjuvant.

In addition, the immunogenic and vaccine compositions of the present invention can include one or more pharmaceutically-acceptable carriers. As used herein, "a pharmaceutically-acceptable carrier" includes any and all solvents, dispersion media, coatings, adjuvants, stabilizing agents, diluents, preservatives, antibacterial and antifungal agents, isotonic agents, adsorption delaying agents, and the like. The carrier(s) must be "acceptable" in the sense of being compatible with the components of the invention and not deleterious to the subject to be immunized. Typically, the carriers will be will be sterile and pyrogen-free.

Part 2 e) Vaccine Dosages and Assays. Dose sizes of H3N8 influenza virus vaccines typically range in volume from about 2.0 to 0.1 ml depending on the route of administration. The inactivated vaccines typically contain between 103 and 109 $TCID_{50}$, levels of virus prior to inactivation. Alternatively the antigen content in the virus preparation would prefer a vaccine with a titer of between 10 to 10,000 HA units/ml, it may have 100 to 2000 HA units/ml, and more preferably has between 100-1000 HA units/ml as the amount administered per dose. For vaccines containing modified live viruses or attenuated viruses, a therapeutically effective dose will generally range from about $10^5$ $TCID_{50}$ to about $10^8$ $TCID_{50}$, inclusive. For vaccines containing subunit antigens, such as influenza H3 or N8 proteins, a therapeutically effective dose generally ranges from about 10 μg to about 100 μg, inclusive. While the amounts and concentrations of adjuvants and additives useful in the context of the present invention can readily be determined by the skilled artisan, the present invention contemplates compositions comprising from about 50 μg to about 2000 μg of adjuvant and preferably about 500 μg/2 ml dose of the vaccine composition.

Assays. Influenza virus can be detected by virus isolation or by viral antigen, viral RNA or specific antibody detection methods. Methods used to detect virus or viral components include immunofluorescence of lung tissue, nasal epithelial cells or bronchioalveolar lavage contents, immunohistochemistry of tissue samples, enzyme linked immunosorbent assay (ELISA), polymerase chain reaction (PCR), cell culture and immunoperoxidase, fluorescent antibody staining for determination of virus type and subtype, and a rapid enzyme-immunoassay membrane test. Tissues typically assessed for influenza virus include lungs, lung lavage, tonsils, trachea, spleen as well as serum. Monoclonal antibodies are also available that specifically target various virus epitopes, namely haemagglutinin (HA) and neuraminidase (NA) epitopes. The most common serologic assay for diagnosis of influenza is the haemagglutinin inhibition (HI) assay. One of its advantages is that it can discriminate between different subtypes and antigenic variants within a subtype. The HI assay can be performed using equine, canine, swine or avian derived sera. A more precise method for measuring antibody is by single radial hemolysis (SRH) technique. SRH is more sensitive than HI assays and has a greater degree of precision. A 50% increase in zone area represents a rise in antibody and is evidence of recent infection.

Part 2 f) Timing and Routes of Administration. Inoculation of a dog is preferably made to a dog that is 6 weeks and more preferably 8 weeks or older. The dogs should receive preferably 2 dosages, each typically administered 3-4 weeks apart, preferably 3 weeks, via subcutaneous injection (SC) depending on the condition of the dog and its environment. This would be to obtain a full, broad immunogenic response. In another embodiment of the present invention, the dog is subjected to a series of 3 vaccinations to produce a full, broad immune response. Annual revaccination with a single dose is recommended. The dogs may optionally be given a booster at 3 and or 6 months if needed. The preferred route is subcutaneous injection, using about 1 mL, but intramuscular (IM), using about 1 mL, or intradermal (ID), using 0.1-0.3 mL, oral, oronasal or nasal routes, using 0.2 to 0.5 mL, are also preferred. Other times, injection sites, amounts used and type of administration will be apparent to one of ordinary skill in the art.

The route of administration for any one of the embodiments of the vaccine of the present invention includes, but is not limited to, intradermal, intramuscular, intraocular, intraperitoneal, intravenous, oral, oronasal, and subcutaneous, as well as inhalation, suppository, or transdermal. The preferred routes of administration include intradermal, intramuscular, intraperitoneal, oronasal, and subcutaneous injection. The vaccine can be administered by any means that includes, but is not limited to, syringes, nebulizers, misters, needleless injection devices, or microprojectile bombardment gene guns (Biolistic bombardment).

Part 3. Specific Descriptions of the Production, Manufacture, Formulation and Administration of Selected Vaccines.

Here we provide more detailed specific descriptions of a killed or inactivated monovalent vaccine, for the treatment of canine influenza.

Part 3a) Killed or Inactivated Virus Monovalent Canine Influenza Vaccine Using any of the antigens described in Part 1 above, including preferred influenza derived H3N8 antigen derived from Canine or Equine Influenza, including inactivated and adjuvanted cultures of H3N8 influenza virus.

Killed or Inactivated Virus Bi-Valent Canine Influenza Vaccine

Using any of the antigens described in Part 1 above, preferably an influenza derived H3N8 antigen derived from Canine and Equine Influenza, inactived and adjuvanted cultures of H3N8 influenza virus. Whereas the canine antigen is derived from one canine influenza virus and the equine antigen is derived from one equine influenza virus. The canine antigen can also consist of two canine influenza viruses or two equine influenza viruses.

Killed or Inactivated Virus Tri-Valent Canine Vaccine

Using any of the antigens described in Part 1 above, but more preferably an influenza derived H3N8 antigen derived from Canine or Equine Influenza, inactivated and adjuvanted cultures of H3N8 influenza virus. The following trivalent vaccines are described: a) A canine antigen is derived from one canine influenza virus and an equine antigen is derived from two equine influenza viruses, b) a canine antigen is derived from two canine influenza viruses and an equine antigen is derived from one equine influenza virus, c) a canine antigen is derived from three canine influenza viruses and or an equine antigen is derived from three equine influenza viruses. Any combination of the above is described in order to make a tri-valent vaccine.

Part 3 b) Killed or Inactivated Vaccine Production and Antigen Concentration. The vaccine described in this section may be produced by growing the selected virus in cells. Production of the virus is preferred in equine or canine mammalian cell culture also preferred is virus (antigen) growth or production in eggs is also preferred. Dog kidney cell lines are more preferred. Viral propagation may also be accomplished on any useful media, including permissive cell lines, which may be derived from feline, equine, bovine, avian or porcine cell lines. The vaccines should contain between $10^5$ and $10^8$ $TCID_{50}$, levels of virus prior to inactivation. Alternatively the virus preparation could be assayed by the Hemagglutination Inhibition (HI) test or hemagglutination assay. Using this assay, one would prefer a vaccine with a titer of between 10 to 10,000 HA units/mL, more typically between 100 to 2000 HA units/mL, and often between 100 to 1000 HA units/mL, as the amount administered.

Killed or Inactivated Virus growth: cell lines and embryonated eggs The preferred cell culture system for growing influenza virus is the traditional adherent monolayer culture. Alternatively, suspension and microcarrier cell culture systems can also be utilized. A preferred microcarrier is Cytodex 3 microcarrier beads (Amersham Biosciences Ltd.). The preferred vessel for culturing cell lines and propagation of influenza virus is the roller bottle format, the preferred roller bottle surface area is 1760 cm² but can range from 850-4250 cm². The preferred multiplicity of infection (MOI) is 0.001-0.1 but can range from 0.0001-2.0. The preferred harvest of virus from cell culture is day 2 to 5 post-infection but can range from day 1 to day 7 post-infection.

Cell culture media: Preferred cell culture media formulations to propagate influenza virus growth includes but are not limited to the following: Dulbecco's modified eagle media (DMEM), basal modified eagle media, Optimem and Leibovitz-15 (L-15) media. Typically the cell culture media is supplemented with 0.1 to 10 units of trypsin.

Part 3c) Killed or Inactivated Inactivation. After production the virus may be killed or inactivated with any method commonly used in the art. A more preferred method would be to inactivate the virus fluids with BEI, described below. Also useful is to inactivate the virus containing fluids with formalin or BPL.

Part 3 d) Killed or Inactivated Vaccine Adjuvants, Formulations, Forms and Carriers. The antigens of Part 1 and in particular the inactivated or killed viruses may be formulated in a variety of ways to produce a useful vaccine. A preferred formulation is to combine killed vaccine with an adjuvant. Numerous adjuvants may be used with the vaccines of this invention, several preferred are noted. The amount of adjuvants typically comprises from about 25 µg to about 1000 µg, inclusive, of a 1 mL dose. Especially useful adjuvants for the Canine Influenza Vaccine are the following, which may also be used in combinations, preferred combinations noted: Aluminum salts, including Alum (0.5-20%, more preferred is less than 10%, more preferred are 2 and 5%), Aluminum phosphate (0.5-20%, more preferred is less than 10%, more preferred are 2 and 5%), Aluminum hydroxide (Alhydrogel or Rehydragel ranging from 0.5-20%, more preferred is less than 10%, more preferred are 2 and 5%), AMPHIGEN® adjuvant, saponins (preferred are Quil A or QS-21 or QA-21 ranging from 1-100 ug Cambridge Biotech Inc., Cambridge Mass.), GPI-0100 (Galenica Pharmaceuticals, Inc., Birmingham, Ala.) with preferred saponin concentrations of 10-100 microgram and about 50 microgram preferred, Cholesterol, or other synthetic polymers, DEAE dextran, Squalene, etc.

Preferred adjuvants and combinations are: 2, 3, 4 or 5% Alum, any combination of Alum with QuilA, Cholesterol, use of any known commercial vaccine adjuvant and formulation. Especially preferred are 2-5% Alum alone, Quil A alone and Quil A and Cholesterol which is known as "QAC." QAC may be used alone or in combination with additional Quil A and Cholesterol. Other known adjuvants may also be used. The other components of the vaccines may be adjusted to modify the physical and chemical properties of the vaccines. For example, adjuvants typically comprise from about 25 µg to about 1000 µg, inclusive, of a 1 mL dose. Similarly, the vaccine described herein could be combined with antibiotics, which may comprise from about 1 µg to about 60 µg, inclusive, of a 1 mL dose. Other ingredients are possible.

Part 3 e) Killed or Inactivated Vaccine Dosages and Assays. Dose sizes of the H3N8 influenza virus vaccines typically range from about 2.0 to 0.1 ml, depending on the route of administration. For vaccines containing modified live viruses or attenuated viruses, a therapeutically effective dose will generally range from about $10^5$ TCID$_{50}$ to about $10^8$ TCID$_{50}$, inclusive. For vaccines containing subunit antigens, such as influenza H3 or N8 proteins, a therapeutically effective dose generally ranges from about 10 µg to about 100 µg, inclusive. For vaccines containing inactivated influenza virus the vaccines should contain between $10^3$ and $10^9$ TCID$_{50}$, levels of virus prior to inactivation. The vaccine will preferably have between 100-1000 HA units/ml as the amount administered per dose. The most preferred is about 640 HA per dose.

Part 3 f) Killed or Inactivated, Timing and Route of Administration. See Part 2 f for the timing of the vaccination. The preferred route is subcutaneous injection, SC, using about 1 mL, but intramuscular, 1M, of about 1 mL or intradermal using 1.0-0.2 mL and oronasal, and nasal using 0.2 to 0.5 mL are also preferred Part 4. Combination of Vaccines The antigens and vaccines of this invention can be combined with other products or vaccines. For example, they can be combined in either the liquid or desiccated fraction with Pfizer's Canine Vanguard® line, which includes many products, and or Pfizer's Canine Vanguard Plus® line, which also includes many products, including Vanguard Plus CCV/L4® and other combinations to offer complete protection against major puppy diseases. The equine or canine influenza virus antigen can be combined in any various combinations with the following canine antigens; canine parainfluenza (CPIV), canine distemper virus (CDV), canine parvovirus (CPV), canine adenovirus-1 (CAV-1), canine adenovirus-2 (CAV-2), *Leptospira canicola, Leptospira grippotyphosa, Leptospira icterohaemorrhagiae, Leptospira pomona, Leptospira bratislava*, canine respiratory coronavirus (CRCV), enteric canine coronavirus (CCV), bovine coronavirus (BCV) and *Bordetella bronchiseptica* antigen.

In addition, the equine or canine influenza virus antigens and vaccines of this invention can be combined with *Bordetella bronchiseptica* (p68 or Bronchicine® or Canvac CCi®) and/or canine parainfluenza (CPIV) and/or canine respiratory coronavirus (CRCV) and/or bovine coronavirus (BCV) vaccines to provide a pre-boarding vaccine to protect against the common agents of kennel cough. Initial dosage of the combination vaccines would be 2 1 mL doses 3 weeks a part, a single 1 mL booster could be given prior to subsequent boardings.

Part 5. Specific Examples of Vaccines

The following vaccines are specifically provided.

EXAMPLES 1-3

Mammalian Cell Grown

Cell derived Pfizer Equine H3N8 (A/Equine/2/Miami/1/1963) in a) 2 or 5% Alum or b) in QAC

EXAMPLES 4-6

Mammalian Cell Grown

Cell derived Pfizer clinical isolate Canine H3N8 A/Canine/Iowa/9A1/B5/D8/D12, in a) 2 or 5% Alum or b) in QAC.

EXAMPLES 7-9

Avian Egg Grown

Egg derived Pfizer Equine H3N8 in a) 2 or 5% Alum or b) in QAC

EXAMPLES 10-11

Avian Egg Grown

Egg derived Pfizer clinical isolate Canine H3N8 in a) 2 or 5% Alum or b) in QAC

Part 6. Specific Examples of Vaccine Testing Procedures

The vaccines of this invention can be evaluated and confirmed using the following.

Purpose bred research dogs 6 weeks of age or older are administered the vaccines described herein. Dogs are allotted into vaccine groups using 5 to 20 dogs per group. Vaccine is administered as two 1 mL doses or two 0.5 mL doses 3 weeks apart via the subcutaneous or intramuscular route. Control dogs are given placebo vaccine. Serum samples are collected from each dog the day of first and second vaccination then twice weekly post second vaccination as well as post challenge. The serum from vaccinated dogs is tested for seroconversion to vaccine antigen via HI (hemagglutinin inhibition) or SRH (single radial hemolysis). Dogs are challenged with H3N8 virus by aerosol or droplets via the intranasal or oral route (which can include intratracheal) at day 14 or day 28 post second vaccination. Dogs are observed post challenge for clinical signs to the disease by monitoring clinical signs such as respiratory symptoms, fever, anorexia, lethargy. Nasal secretions are collected by swabbing vaccinated dogs and non-vaccinated controls every other day post challenge for 10-14 days to measure shedding of challenge virus. Presence of shedding virus is confirmed by cell tissue culture (preferably dog kidney). Tissue samples including trachea, tonsil, lung are collected from a subset of dogs post challenge. The presence of virus in dog tissue samples is confirmed as described above or immunohistochemical analysis. By comparing shedding of challenge virus and virus in tissue samples, dogs vaccinated with an effective vaccine will have a lower virus load or lower virus amount as compared to non-vaccinated control dogs. An effective vaccine will result in lower virus load or lower virus amount in a vaccinated animal and vaccinated animals will demonstrate a reduction in clinical signs associated with influenza infection as compared to an non-vaccinated control.

SPECIFIC EXAMPLES

Challenge and Efficacy Study Evaluation of Canine Influenza Vaccines in Dogs. Evaluation of equine Influenza Vaccine, Killed Virus to Provide Cross-Protection in Canines Against Influenza Virus.

To evaluate seroprotection of equine influenza viruses; A/Equine/2/Miami/1/63 and A/Equine/Ohio/1/2003 containing vaccines, 7-10 week old dogs were allotted into one of nine treatment groups (Table 1). Dogs were vaccinated with a 1.0 mL dose via the subcutaneous route on Study Days 0 and 21. Blood for serum was collected from all dogs enrolled in the study on Study Days 0 (first vaccination), 21 (second vaccination) and 35 (14 days post second vaccination). All serum samples were assayed for HAI to Miami63, Ohio03, and CIV. The serological response data are presented in Table 2. Statistically significant differences in serological titers compared to non-vaccinated animals were demonstrated on Study Day 35 in the following IVP groups: T02, T03, T04, T06, T07, T08, and T09 (Table 2). Additionally, statistically significant differences were observed on Study Day 21 for the following IVP groups: T06, T07, T08, and T09 (Table 2).

Preliminary Safety

In addition to measuring serological response, preliminary vaccine safety was evaluated in this study. Over all, no clinically important vaccine associated reactions were observed with any of the IVPs evaluated. No vaccine associated systemic reactions were observed during the course of the study. Additionally, no injection site swellings were observed following the first vaccination in any of the treatment groups (Table 3). On Day 21 (prior to $2^{nd}$ vaccination), small swellings were detected upon palpation of the injection site in 34 animals from five treatment groups. Of these groups, four (T02, T03, T06, and T07) are adjuvanted with 2% Alum, while the fifth treatment group (T09) is adjuvanted with Quil-A/Cholesterol/Plus other adjuvants. The geometric mean volume on this Day 21 swelling ranged in size from 0.07 to 0.24 $cm^3$ across treatments.

Following the second vaccination, Study Days 22-24, injection site swellings were observed in 58 of 87 animals. These swellings peaked 24 hours following vaccination (Day 22) and decreased in size toward resolution until Study Day 24. None of the injection site swellings were painful or hot to touch, while five were found to be hard to tough.

Evaluation of equine Influenza Vaccine, Killed Virus to Provide Cross-Protection in Canines Against Influenza Virus By Challenge Six of the nine treatment groups were challenged with CIV: T01, T02, T03, T06, T07, and T09. Study Day 0, day of challenge, animals 6 weeks after the second vaccination with approximately HA of 1:8 per 50 ml representing approximately 6.9 logs per mL of CIV. Dogs were challenged via the intratracheal route in a model similar to the swine influenza virus respiratory disease model. Clinical signs associated with respiratory disease were observed daily on all animals: nasal discharge, ocular discharge, sneezing, retching, anorexia, depression, or coughing. Additionally, tympanic temperatures and nasal/pharyngeal swabs for virus isolation were collected daily.

Clinical observations were reported and tracked daily until approximately 50% of the challenged animals exhibited clinical signs of respiratory disease. Five days post-challenge, 31 of 59 challenged animals exhibited one or more of the following clinical signs: nasal discharge, ocular discharge and/or coughing. Therefore, on Study Day 5, all animals were euthanized and necropsies performed. Lung consolidation scores were recorded and samples for virus isolation collected.

The percent lung consolidation scores indicated that successful demonstration of respiratory disease was achieved with this challenge, Percent consolidation across all animals ranged from 60% in 9 animals, to eight animals with 10 to 35% consolidation, 26 animals exhibiting <10% consolidation and 16 animals exhibiting no consolidation (FIG. 2). Numbers of animals with lung consolidation across treatment groups are presented in Table 4. While numeric differences were observed between treatment groups and negative controls, statistically significant differences for lung consolidation, virus isolation in lung and tonsil tissues were not detected (Table 5). From lung lavage samples, statistically significant differences ($P<=0.05$) were detected in the virus isolation results between negative controls and T02, T07, and T09 (Table 6).

TABLE 1

Treatment groups for canine seroconversion study.

| Group | IVP |
|---|---|
| T01 | Saline - Negative Control |
| T02 | Miami 63 - 320 HAI dose - 2% Alum |
| T03 | Miami 63 - 640 HAI dose - 2% Alum |
| T04 | Miami 63 - 320 HAI dose - Quil-A/Cholesterol |
| T05 | Miami 63 - 640 HAI dose - Quil-A/Cholesterol |
| T06 | Ohio 03 - 320 HAI dose - 2% Alum |
| T07 | Ohio 03 - 640 HAI dose - 2% Alum |
| T08 | Ohio 03 - 640 HAI dose - Quil-A/Cholesterol |
| T09 | Ohio 03 - 640 HAI dose - Quil-A/Cholesterol/plus other adjuvants |

TABLE 2

Serological Titer Data Summary in dogs vaccinated with equine influenza antigen vaccines (36252)
HAI titers against CIV

| Treatment group | | | Day 0 | Day 21 Geometric | | | Day 35 | | |
|---|---|---|---|---|---|---|---|---|---|
| Group | IVP | N | Actual | Mean | Min | Max | GM | Min | Max |
| T01 | Saline | 10 | <8 | 4.0 | 4.0 | 4.0 | 4.0 | 4.0 | 4.0 |
| T02 | Miami 63 - low dose - 2% Alum | 9 | <8 | 4.0 | 4.0 | 4.0 | 9.3* | 4.0 | 16.0 |
| T03 | Miami 63 - high dose - 2% Alum | 10 | <8 | 4.0 | 4.0 | 4.0 | 12.1* | 4.0 | 128.0 |
| T04 | Miami 63 - low dose - Quil-A/Cholesterol | 10 | <8 | 4.0 | 4.0 | 4.0 | 9.2* | 4.0 | 16.0 |
| T05 | Miami 63 - high dose - Quil-A/Cholesterol | 8 | <8 | 4.0 | 4.0 | 4.0 | 7.3 | 4.0 | 16.0 |
| T06 | Ohio 03 - low dose - 2% Alum | 10 | <8 | 17.1* | 8.0 | 64.0 | 48.5* | 32.0 | 128.0 |
| T07 | Ohio 03 - high dose - 2% Alum | 10 | <8 | 11.3* | 4.0 | 32.0 | 55.7* | 32.0 | 128.0 |
| T08 | Ohio 03 - high dose - Quil-A/Cholesterol | 10 | <8 | 7.5* | 4.0 | 16.0 | 18.4* | 8.0 | 32.0 |
| T09 | Ohio 03 - high dose - Quil-A/plus other adjuvants | 10 | <8 | 32.0* | 4.0 | 128.0 | 84.4* | 8.0 | 256.0 |

*= Significant difference between T01 and marked group (P ≦ 0.05)

TABLE 3

Frequency Distribution of Positive Injection Site Reactions on Each Study Day by Treatment Group

| Treatment group | | Positive Injection Site Reactions | | | | | | |
|---|---|---|---|---|---|---|---|---|
| Group | IVP | D0 | D2 | D3 | D21 | D22 | D23 | D24 |
| T01 | Saline | 0 | 0 | 0 | 0 | 0 | 0 | 0 |
| T02 | Miami 63 - low dose - 2% Alum | 0 | 0 | 0 | 8/8 | 7/9 | 8/9 | 7/9 |
| T03 | Miami 63 - high dose - 2% Alum | 0 | 0 | 0 | 8/10 | 10/10 | 6/9 | 8/9 |
| T04 | Miami 63 - low dose - Quil-A/Cholesterol | 0 | 0 | 0 | 0 | 6/10 | 6/10 | 5/10 |
| T05 | Miami 63 - high dose - Quil-A/Cholesterol | 0 | 0 | 0 | 0 | 6/9 | 5/8 | 5/8 |
| T06 | Ohio 03 - low dose - 2% Alum | 0 | 0 | 0 | 6/10 | 10/10 | 7/8 | 9/9 |
| T07 | Ohio 03 - high dose - 2% Alum | 0 | 0 | 0 | 7/10 | 9/10 | 10/10 | 9/10 |
| T08 | Ohio 03 - high dose - Quil-A/Cholesterol | 0 | 0 | 0 | 0 | 0 | 0 | 0 |
| T09 | Ohio 03 - high dose - Quil-A/Cholesterol/plus other adjuvants | 0 | 0 | 0 | 5/10 | 10/10 | 10/10 | 8/9 |

TABLE 4

Number of animals per treatment group with positive lung consolidation scores.

| | IVP | | | | |
|---|---|---|---|---|---|
| | T01 | T02 | T03 | T06 | T07 | T09 |
| No. Positive | 8 | 5 | 9 | 7 | 5 | 9 |
| No. Negative | 2 | 4 | 1 | 3 | 5 | 1 |

TABLE 5

Virus Isolation from Lung and Tonsil Samples by Treatment Group

| | Virus Isolated? Yes/No | | | | | | | |
|---|---|---|---|---|---|---|---|---|
| | Lung | | | | Tonsil | | | |
| | No | | Yes | | No | | Yes | |
| IVP | No. | % | No. | % | No. | % | No. | % |
| T01 | 7 | 70.0 | 3 | 30.0 | 9 | 90.0 | 1 | 10.0 |
| T02 | 8 | 88.9 | 1 | 11.1 | 9 | 100.0 | 0 | 0 |
| T03 | 10 | 100.0 | 0 | 0 | 10 | 100 | 0 | 0 |

TABLE 5-continued

Virus Isolation from Lung and Tonsil Samples by Treatment Group

| | Virus Isolated? Yes/No | | | | | | | |
|---|---|---|---|---|---|---|---|---|
| | Lung | | | | Tonsil | | | |
| | No | | Yes | | No | | Yes | |
| IVP | No. | % | No. | % | No. | % | No. | % |
| T06 | 9 | 90.0 | 1 | 10.0 | 9 | 90.0 | 1 | 10.0 |
| T07 | 10 | 100.0 | 0 | 0 | 10 | 100.0 | 0 | 0 |
| T09 | 10 | 100.0 | 0 | 0 | 10 | 100.0 | 0 | 0 |

TABLE 6

Virus Isolation from Lung Lavage Samples by Treatment Group.

| | Virus Isolated? Yes/No | | | |
|---|---|---|---|---|
| | No | | Yes | |
| IVP | Number | Percentage | Number | Percentage |
| T01 | 2 | 20.0 | 8 | 80.0 |
| T02 | 7 | 77.8 | 2 | 22.2* |
| T03 | 5 | 50.0 | 5 | 50.0 |
| T06 | 7 | 70.0 | 3 | 30.0* |
| T07 | 10 | 100.0 | 0 | 0* |
| T09 | 10 | 100.0 | 0 | 0* |

*Indicates statistically significant difference ($p \leq 0.05$) between T01 and treatment group

CONCLUSION OF SPECIFIC DESCRIPTIONS

It should be noted that, as used in this specification and the appended claims, singular articles such as "a," "an," and "the," may refer to one object or to a plurality of objects unless the context clearly indicates otherwise. Thus, for example, reference to a composition containing "a compound" may include a single compound or two or more compounds.

It is to be understood that the above description is intended to be illustrative and not restrictive. Many embodiments will be apparent to those of skill in the art upon reading the above description. The scope of the invention should, therefore, be determined with reference to the appended claims, along with the full scope of equivalents to which such claims are entitled. The disclosures of all articles and references, including patents, patent applications and publications, are incorporated herein by reference in their entirety and for all purposes.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

The invention claimed is:

1. A method of preventing or reducing a disease in a dog caused by a subtype H3 influenza virus, the method comprising administering to the dog a therapeutically effective amount of a vaccine containing at least one influenza virus, wherein said virus is isolated from a dog, is subtype H3N8, and is killed, wherein said influenza virus consists of that deposited with the American Type Culture Collection (ATCC) as PTA-7694, and wherein said vaccine further comprises at least one antigen selected from the group consisting of canine parainfluenza (CPIV), canine distemper virus (CDV), canine parvovirus (CPV), and canine adenovirus-2 (CAV-2).

2. The method of claim 1, wherein said vaccine further comprises enteric canine coronavirus (CCV).

3. A method of preventing or reducing a disease in a dog caused by a subtype H3 influenza virus, the method comprising administering to the dog a therapeutically effective amount of a vaccine containing at least influenza virus, wherein said virus is isolated from a dog. is subtype H3N8, and is killed, wherein said influenza virus consists of that deposited with the American Type Culture Collection (ATCC) as PTA-7694, and wherein said vaccine further comprises at least one antigen selected from the group consisting of *Leptospira canicola, Leptospira grippotyphosa, Leptospira icterohaemorrhagiae, Leptospira pomona*, and *Leptospira bratislava*.

4. The method of claim 1, wherein said vaccine further comprises at least one antigen selected from the group consisting of *Leptospira canicola, Leptospira grippotyphosa, Leptospira icterohaemorrhagiae, Leptospira pomona*, and *Leptospira bratislava*.

5. The method of claim 2, wherein said vaccine further comprises at least one antigen selected from the group consisting of *Leptospira canicola, Leptospira grippotyphosa, Leptospira icterohaemorrhagiae, Leptospira pomona*, and *Leptospira bratislava*.

* * * * *